United States Patent

Roe et al.

[11] Patent Number: 5,968,025
[45] Date of Patent: *Oct. 19, 1999

[54] ABSORBENT ARTICLE HAVING A LOTIONED TOPSHEET

[75] Inventors: Donald Carroll Roe; Frank Heinrich Bakes; Alrick Vincent Warner, all of Cincinnati, Ohio

[73] Assignee: The Procter & Gamble Company, Cincinnati, Ohio

[*] Notice: This patent is subject to a terminal disclaimer.

[21] Appl. No.: 08/884,575

[22] Filed: Jun. 27, 1997

Related U.S. Application Data

[63] Continuation of application No. 08/345,159, Nov. 28, 1994, Pat. No. 5,643,588.

[51] Int. Cl.$^6$ .................................................. A61F 13/15
[52] U.S. Cl. ........................ 604/364; 604/360; 604/367
[58] Field of Search .................... 604/358, 359, 604/360, 363, 364, 376, 378, 381, 385.1; 424/402, 443

[56] References Cited

U.S. PATENT DOCUMENTS

| | | | |
|---|---|---|---|
| 3,489,148 | 1/1970 | Duncan et al. | 604/382 |
| 3,490,454 | 1/1970 | Goldfarb et al. | 604/359 |
| 3,585,998 | 6/1971 | Hayford | 604/359 |
| 3,875,942 | 4/1975 | Roberts et al. | 128/287 |
| 3,896,807 | 7/1975 | Buchalter | 604/289 |
| 4,263,363 | 4/1981 | Buck et al. | |
| 4,569,343 | 2/1986 | Kimura et al. | |
| 4,623,339 | 11/1986 | Ciraldo et al. | 604/359 |
| 4,666,765 | 5/1987 | Caldwell et al. | |
| 4,748,978 | 6/1988 | Kamp | 604/359 |
| 4,753,643 | 6/1988 | Kassai | 604/359 |
| 4,790,836 | 12/1988 | Brecher | 604/359 |
| 4,959,059 | 9/1990 | Eilender et al. | 604/358 |
| 5,264,460 | 11/1993 | Jakobson et al. | |
| 5,321,098 | 6/1994 | Lal | |
| 5,415,649 | 5/1995 | Watanabe et al. | |
| 5,609,587 | 3/1997 | Roe | 604/360 |
| 5,635,191 | 6/1997 | Roe et al. | 424/402 |
| 5,643,588 | 7/1997 | Roe et al. | 604/360 |

FOREIGN PATENT DOCUMENTS

| | | |
|---|---|---|
| 2019557 | 6/1990 | Canada . |
| 4136540 A1 | 11/1991 | Germany . |
| 61/028078 | 2/1986 | Japan . |
| 2-31756 | 2/1990 | Japan . |
| 05/285170 | 4/1992 | Japan . |
| 8-52175 | 2/1996 | Japan . |

*Primary Examiner*—Mark O. Polutta
*Attorney, Agent, or Firm*—Bart S. Hersko; Carl J. Roof; Jeffrey V. Bamber

[57] ABSTRACT

An absorbent article containing a liquid pervious topsheet coated with a lotion composition is disclosed. The lotion composition comprises a plastic or fluid emollient such as mineral oil or petrolatum, an immobilizing agent such as a fatty alcohol or paraffin wax to immobilize the emollient on the surface of the topsheet, and optionally a hydrophilic surfactant to improve wettability of the coated topsheet. Because the emollient is substantially immobilized on the surface of the topsheet, less lotion is required to impart the desired therapeutic or protective lotion coating benefits.

25 Claims, 3 Drawing Sheets

ABSORBENT ARTICLE HAVING A LOTIONED TOPSHEET

This is a continuation of application Ser. No. 08/345,159, filed on Nov. 28, 1994 now U.S. Pat. No. 5,643,588.

TECHNICAL FIELD

This application relates to absorbent articles such as diapers, training pants, adult incontinence devices, and the like. More particularly, the present invention relates to absorbent articles having a lotion coating on the outer surface of the topsheet that is transferable to the wearer's skin by normal contact and wearer motion and/or body heat. The lotions disclosed in the present invention reduce the adherence of BM to the skin of the wearer, thereby improving the ease of BM clean up.

BACKGROUND OF THE INVENTION

Many types of disposable absorbent products, such as diapers, are available that have a high capacity for absorbing urine. Disposable products of this type generally comprise some sort of fluid-permeable topsheet material, an absorbent core, and a fluid-impermeable backsheet material. Although these types of absorbent structures may be highly efficient for the absorption of fluids, they cannot absorb bowel movements (i.e., hereinafter referred to as "BM"). Typically, the BM is trapped between the outer surface of the fluid-permeable topsheet and the skin of the wearer, much of it adhering to the wearer's skin.

To prevent BM from adhering to the wearer's skin, the caregiver often applies protective or "repellent" products such as vaseline or mineral oil to the buttocks and anal region before placing the absorbent article on the wearer. This procedure usually involves the caregiver's pouring of the oil or lotion, for example, in one of their hands, rubbing both hands together to distribute the substance thereon and then wiping the same on the skin of the infant. To eliminate the need for this wasteful, messy, and easily forgotten procedure, there have been numerous previous attempts to prepare absorbent articles which contain a protective or therapeutic skin care substance on the topsheet.

One substance that has been applied as a lotion to diaper products to impart a soothing, protective coating is mineral oil. Mineral oil (also known as liquid petrolatum) is a mixture of various liquid hydrocarbons obtained by distilling the high-boiling (i.e., 300°–390° C.) fractions in petroleum. Mineral oil is liquid at ambient temperatures, e.g. 20°–25° C. As a result, mineral oil is relatively fluid and mobile, even when applied to diaper topsheets.

Because mineral oil is fluid and mobile at ambient temperatures, it tends not to remain localized on the surface of the topsheet, but instead migrates through the topsheet into the interior of the diaper. Accordingly, relatively high levels of mineral oil need to be applied to the topsheet to provide the desired therapeutic or protective coating lotion benefits. This leads not only to increased costs for these lotioned diaper products, but other detrimental effects as well.

One of these detrimental effects is a decrease in the fluid handling properties as high levels of mineral oil tend to block the topsheet openings. Also, as mineral oil migrates to the interior of the diaper, it tends to act as a hydrophobic additive, thus decreasing the absorbency of the underlying absorbent core, if one is used. This decrease in absorbency becomes more pronounced as the level of mineral oil applied is increased.

Even without increasing its level, the tendency of mineral oil to migrate once applied has other detrimental effects. For example, the applied mineral oil can transfer to, into and through the packaging or wrapper material for the lotioned diaper product. This can create the need for barrier-type packaging or wrapper films to avoid smearing or other leakage of mineral oil from the diaper product.

Accordingly, it would be desirable to provide lotioned diaper products that: (1) have desirable therapeutic or protective coating lotion benefits (2) do not require relatively high levels of coatings that are liquid at room temperature (e.g., mineral oil) (3) do not adversely affect the absorbency of the diaper product; and (4) do not require special wrapping or barrier materials for packaging.

U.S. Pat. No. 3,585,998 to Hayford et al. teaches a disposable baby diaper, an interior liner of which carries an array of pressure-rupturable capsules containing baby oil. The patent teaches that it is desirable to break the capsules prior to using the diaper by applying pressure with such household items as a rolling pin, hand iron, etc. The same principle of pressure-rupturable capsules is used in U.S. Pat. No. 3,464,413 to Goldfarb et al. for making bandages capable of delivering a medicinal material to an injury. Articles disclosed by both patents have a serious drawback Namely, unless the capsules are ruptured by applying pressure prior to using the diaper or the bandage, the skin-care substance contained in the capsules is either not delivered at all or is delivered non-uniformly leaving some areas of skin uncoated.

U.S. Pat. No. 3,896,807 to Buchalter teaches an article impregnated with a solid oil phase of cream formulation which forms a cream upon addition of moisture thereto. A major disadvantage of the article disclosed by the reference is that transfer of a beneficial substance from the absorbent substrate to skin is delayed and is only realized when body fluids are released.

U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores.

Therefore, it is an object of the present invention to provide a disposable diaper having a hydrophilic topsheet having superior fluid handling properties.

It is a further object of the present invention to provide a hydrophilic diaper topsheet having a lotion coating on the outer surface of the topsheet that is transferable to the wearer's skin and is effective at reducing the adherence of BM to the skin, thereby improving the ease of BM cleanup.

It is yet a further object of the present invention desirable to provide lotioned diaper products that: (1) have desirable BM release, cleaning, therapeutic or protective lotion coating benefits (2) do not require relatively high levels of mineral oil; (3) do not adversely affect the fluid handling properties of the diaper; and (4) do not require special wrapping or barrier materials for packaging.

These and other objects are obtained using the present invention, as will become readily apparent from a reading of the following disclosure.

SUMMARY OF THE INVENTION

The present invention relates to a disposable absorbent article having a lotion coating on the outer surface of the topsheet that is semisolid or solid at ambient temperatures (i.e., at 20° C.) and is adapted to be transferred to the wearer's skin.

Briefly, the disposable absorbent articles of the present invention comprise:

A) a liquid impervious backsheet;
B) a liquid pervious, hydrophilic topsheet joined to said backsheet, said topsheet having an inner surface oriented toward the interior of said absorbent articles and an outer surface oriented toward the skin of the wearer when said absorbent articles is being worn, wherein at least a portion of said topsheet outer surface comprises an effective amount of a lotion coating which is semisolid or solid at 20° C. and which is partially transferable to the wearer's skin, said lotion coating comprising:
  (i) from about 10 to about 95% of a substantially water free emollient having a plastic or fluid consistency at 20° C. and comprising a member selected from the group consisting of petroleum-based emollients, fatty acid ester emollients, alkyl ethoxylate emollients, polysiloxane emollients, and mixtures thereof;
  (ii) from about 5 to about 90% of an agent capable of immobilizing said emollient on said outer surface of the topsheet, said immobilizing agent having a melting point of at least about 35° C.; and
C) an absorbent core positioned between said topsheet and said backsheet.

The quantity of lotion coating on a least a portion of the topsheets preferably ranges from about 0.1 mg/in$^2$ to about 25 mg/in$^2$, more preferably from about 1 mg/in$^2$ to about 10 mg/in$^2$. Lotioned topsheets according to the present invention provide desirable BM cleaning, therapeutic or protective lotion coating benefits. Because the emollient is substantially immobilized on the surface of the topsheet, less lotion composition is needed to impart the desired skin care benefits. In addition, special barrier or wrapping materials are unnecessary in packaging the lotioned absorbent articles of the present invention.

As will be discussed hereinafter, the lotion compositions of the present invention preferably have a melting profile such that they are relatively immobile and localized on the topsheet at room temperature, are transferable to the wearer at body temperature, and yet are not completely liquid under extreme storage conditions. importantly, the lotion compositions of the present invention are easily transferable to the skin by way of normal contact, wearer motion, and/or body heat. Without being bound by theory, it is believed that the lotion composition changes the surface energy of the skin, and/or forms a "barrier" reducing the affinity of the skin for BM. The BM, therefore, has a reduced tendency to stick to the skin, and is easier to remove.

DETAILED DESCRIPTION OF THE INVENTION

Figure 1:
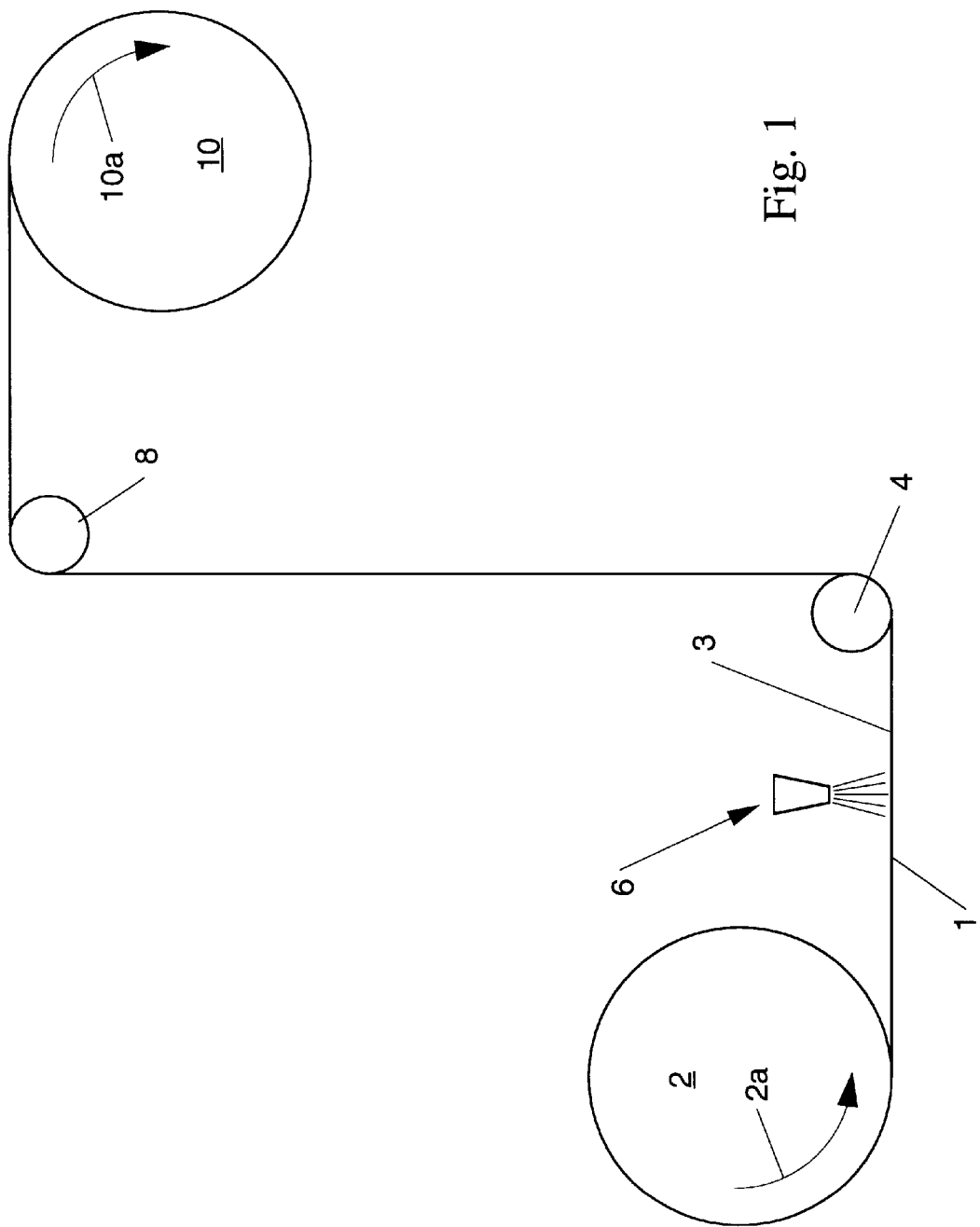
FIG. 1 is a schematic representation illustrating a preferred process for applying the lotion composition of the present invention to diaper topsheets.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

A. Absorbent Article

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles include feminine hygiene garments such as sanitary napkins and panti-liners, diapers, incontinence briefs, diaper holders, training pants, and the like.

Disposable absorbent articles typically comprise a liquid pervious topsheet, a liquid impervious backsheet joined to the topsheet and an absorbent core positioned between the topsheet and the backsheet.

Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn toward or placed adjacent to the wearer's body or undergarments when the disposable absorbent article is worn.

The following description generally discusses the absorbent core, topsheet, and backsheet materials that are useful in disposable absorbent articles. It is to be understood that this general description applies to these components of the specific absorbent articles shown in FIG. 3 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer, or a secondary topsheet for increasing the wearer's comfort.

The topsheet is preferably compliant, soft feeling, and non-irritating to the wearers skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Indiana, under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment means (not shown in FIG. 3) such as those well known in the art. However, embodiments of the present invention are envisioned wherein portions of the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on October 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the lotioned topsheets of the present invention may be used are diapers. As used herein, the term "diaper" refers to an absorbent article generally worn by infants, and incontinent persons that is worn about the lower torso of the wearer. In other words, the term "diaper" includes infant diapers, training pants, adult incontinence devices, etc.

Figure 3:
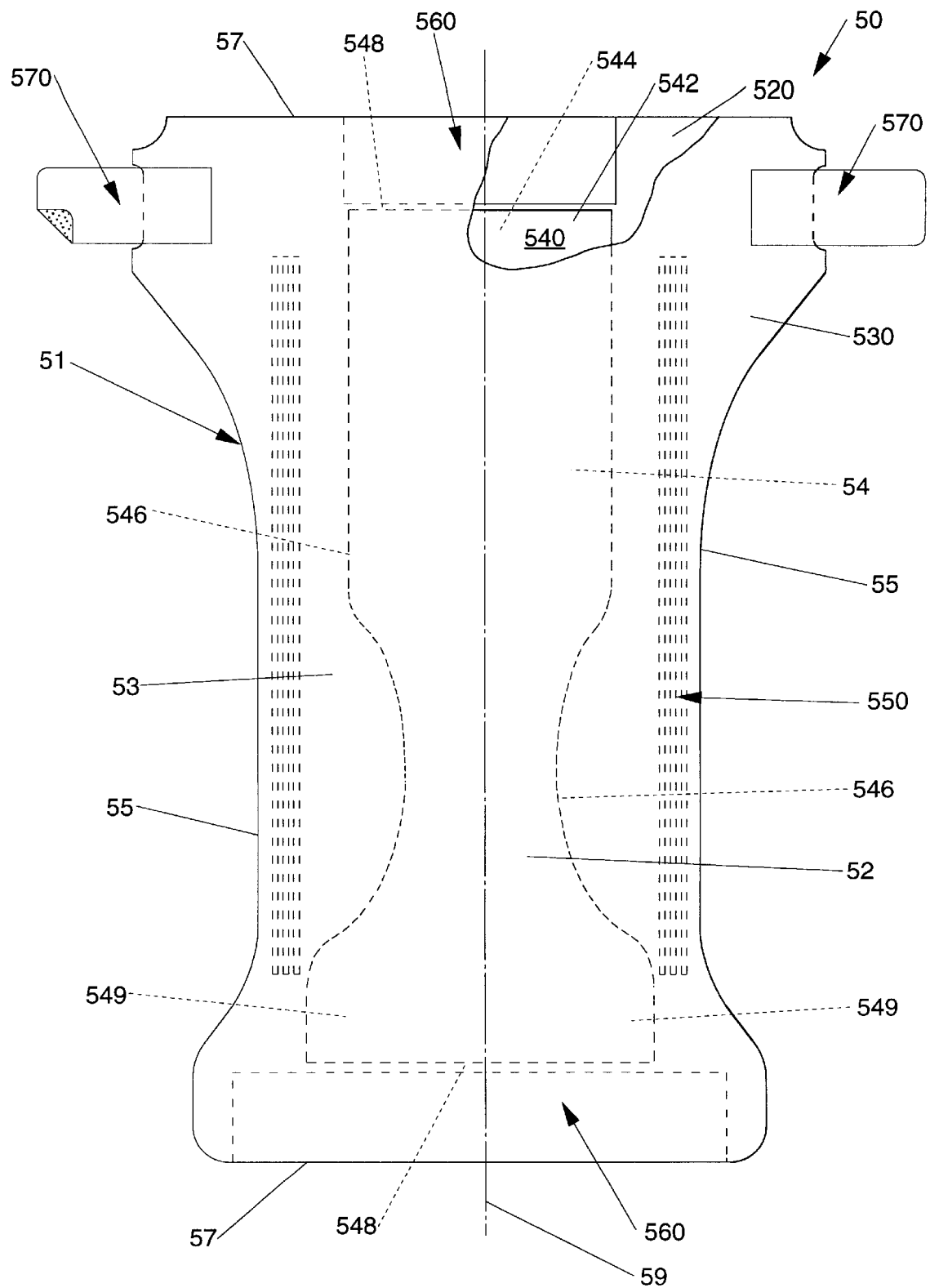
FIG. 3 is an absorbent article in the form of a diaper according to the present invention.

FIG. 3 is a plan view of the diaper 50 of the present invention in its flat-out, uncontracted state (i.e., with elastic induced contraction pulled out) with portions of the structure being cut-away to more clearly show the construction of the diaper 50 and with the portion of the diaper 50 which faces away from the wearer, the outer surface, oriented towards the viewer. As shown in FIG. 3, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550; an elastic waist feature multiply designated as 560; and a fastening system generally multiply designated as 570.

The diaper 50 is shown in FIG. 3 to have an outer surface 52, an inner surface 54 opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The inner surface 54 of the diaper 50 comprises that portion of the diaper 50 which is positioned adjacent to the wearer's body during use (i.e., the inner surface 54 generally is formed by at least a portion of the topsheet 520 and other components that may be joined to the topsheet 520 ). The outer surface 52 comprises that portion of the diaper 50 which is positioned away from the wearer's body (i.e., the outer surface 52 generally is formed by at least a portion of the backsheet 530 and other components that may be joined to the backsheet 530 ). (As used herein, the portion of the diaper 50 or component thereof which faces the wearer is also referred to as the body facing surface. Similarly, the portion facing away from the wearer is also referred to herein as the garment facing surface.) The first waist region 56 and the second waist region 58 extend, respectively, from the end edges 57 of the periphery 51 to the lateral centerline 53 of the diaper 50. FIG. 3 also shows the longitudinal centerline 59.

FIG. 3 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted are described in co-pending U.S. patent application Ser. Nos. 08/203,456; filed on Feb. 28, 1994 and incorporated herein by reference. The absorbent cores of diapers described in these patents can be adapted in light of the teachings herein to include the absorbent composite of the present invention as an absorbent gelling material described therein.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of a diaper as described herein, the backsheet 530 has a modified hourglass shape extending beyond the absorbent core a minimum distance of about 1.3 cm to about 6.4 (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent structures for use as the absorbent core of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized side panels (not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each being incorporated herein by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S.

Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

The lotioned topsheets of the present invention are also useful in training pants. The term "training pants", as used herein, refers to disposable garments having fixed sides and leg openings. Training pants are placed in position on the wearer by inserting the wearers legs into the leg openings and sliding the training pant into position about the wearer's lower torso. Suitable training pants are disclosed in U.S. Pat. No. 5,246,433, issued to Hasse, et al. on Sep. 21, 1993.

Another disposable absorbent article for which the lotioned topsheets of the present invention are useful are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992).

B. Lotion Composition

The lotion compositions of the present invention are solid, or more often semisolid, at 20° C., i.e. at ambient temperatures. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components.

The lotion compositions of the present invention are at least semisolid solid at room temperature to minimize lotion migration. In addition, the compositions preferably have a final melting point (100% liquid) above potential "stressful" storage conditions that can be greater than 45° C. (e.g., warehouse in Arizona, car trunk in Florida, etc.).

Specifically, the lotion compositions of the present invention should have the following melt profile:

| Characteristic | Preferred Range | Most Preferred |
|---|---|---|
| % liquid at room temp. (20° C.) | 2–50 | 3–25 |

-continued

| Characteristic | Preferred Range | Most Preferred |
|---|---|---|
| % liquid at body temp. (37° C.) | 25–95 | 30–90 |
| final melting point (°C.) | ≧35 | ≧45 |

By being solid or semisolid at ambient temperatures, these lotion compositions do not have a tendency to flow and migrate into the interior of the diaper topsheet to which they are applied. This means less lotion composition is required for imparting desirable therapeutic or protective coating lotion benefits.

When applied to outer surface of diaper topsheets, the lotion compositions of the present invention are transferable to the wearers skin by normal contact, wearer motion, and/or body heat. Importantly, the lotions disclosed in the present invention reduce the adherence of BM to the skin of the wearer, thereby improving the ease of BM clean up.

The diaper topsheets of the present invention contain an effective amount of the lotion composition. As used herein, the term "effective amount of a lotion coating" refers to an amount of a particular lotion composition which, when applied to a diaper topsheet, will be effective in reducing the adherence of BM to the skin of the wearer. Of course, the effective amount of a lotion coating will depend, to a large extent, on the particular lotion composition used.

The lotion compositions of the present invention comprise: (1) an emollient(s); (2) an immobilizing agent(s) for the emollient; (3) optionally a hydrophilic surfactant(s); and (4) other optional components.

The viscosity of the formulated lotion compositions, including emollient, immobolizing agent, and optional components should be as high as possible to keep the lotion from flowing into the interior of the diaper. Unfortunately, high viscosities can also lead to lotion compositions that are difficult to apply without processing problems. Therefore, a balance must be achieved so the viscosities are high enough to keep the lotion compositions localized on the surface of the diaper topsheet, but not so high as to cause processing problems. Suitable viscosities for the lotion compositions will typically range from about 5 to about 200 centipoises, preferably from about 15 to about 100 centipoises, measured at 60° C.

1. Emollient

The key active ingredient in these lotion compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. For the purposes of the present invention, these emollients have either a plastic or fluid consistency at 20° C., i.e., at ambient temperatures. This particular emollient consistency allows the lotion composition to impart a soft, lubricious, lotion-like feel.

The emollients useful in the present invention are also substantially free of water. By "substantially free of water" is meant that water is not intentionally added to the emollient. Addition of water to the emollient is not necessary in preparing or using the lotion compositions of the present invention and could require an additional drying step. However, minor or trace quantities of water in the emollient that are picked up as a result of, for example, ambient humidity can be tolerated without adverse effect. Typically, the emollients used in the present invention contain about 5% or less water, preferably about 1% or less water, most preferably about 0.5% or less water.

Emollients useful in the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for lotion compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol thoxylate having an average degree of ethoxylation of 10). These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use in the present invention include polysiloxane compounds. In general suitable polysiloxane materials for use in the present invention include those having monomeric siloxane units of the following structure:

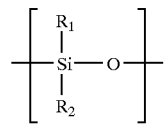

(1)

wherein, $R_1$ and $R_2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit. Additionally, the polysiloxane can be either a straight chain, a branched chain or have a cyclic structure. The radicals $R_1$ and $R_2$ can additionally independently be other silaceous functionalities such as, but not limited to siloxanes, polysiloxanes, silanes, and polysilanes. The radicals $R_1$ and $R_2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the diaper topsheet. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the diaper topsheets by such methods as, for example, emulsifying the polysiloxane in surfactant or providing the polysiloxane in solution with the aid of a solvent, such as hexane, listed for exemplary purposes only. Particular methods for applying polysiloxane emollients to diaper topsheets are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the lotion compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petroleum-based emollients, fatty acid ester emollients, fatty acid ester ethoxylates, alkyl ethoxylate emollients fatty alcohol emollients, and polysiloxanes, the emollients useful in the present invention can include minor amounts (e.g., up to about 10% of the total emollient) of other, conventional emollients. These other, conventional emollients include propylene glycol, glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$–$C_{28}$ fatty acids; other fatty esters of polyhydroxy alcohols; lanolin and its derivatives. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 10 to about 95% of the emollient. Preferably, the lotion composition comprises from about 20 to about 80%, most preferably from about 40 to about 75%, of the emollient.

2. Immobilizing Agent

An especially key component of the lotion compositions of the present invention is an agent capable of immobilizing the emollient on the diaper topsheet to which the lotion composition is applied. Because the emollient in the composition has a plastic or fluid consistency at 20° C., it tends to flow or migrate, even when subjected to modest shear. When applied to a diaper topsheet, especially in a melted or molten state, the emollient will not remain primarily on the surface of the topsheet. Instead, the emollient will tend to migrate and flow into the interior of the diaper.

This migration of the emollient into the interior of the diaper can cause undesired effects on the absorbency of the diaper core due to the hydrophobic characteristics of many of the emollients used in the lotion compositions of the present invention. It also means that much more emollient has to be applied to the diaper topsheet to get the desired therapeutic or protective lotion benefits. Increasing the level of emollient not only increases the cost, but also exacerbates the undesirable effect on the absorbency of the diaper core.

The immobilizing agent counteracts this tendency of the emollient to migrate or flow by keeping the emollient primarily localized on the surface of the diaper topsheet to which the lotion composition is applied. This is believed to be due, in part, to the fact that the immobilizing agent raises the melting point of the lotion composition above that of the emollient. Since the immobilizing agent is also miscible with the emollient (or solubilized in the emollient with the aid of an appropriate emulsifier), it entraps the emollient on the surface of the diaper topsheet as well.

It is also advantageous to "lock" the immobilizing agent on the surface of the diaper topsheet. This can be accomplished by using immobilizing agents which quickly crystallize (i.e., solidify) at the surface of the topsheet. In addition, outside cooling of the treated diaper topsheet via blowers, fans, etc. can speed up crystallization of the immobilizing agent.

In addition to being miscible with (or solubilized in) the emollient, the immobilizing agent needs to have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

Suitable immobilizing agents for the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear.

Importantly, these preferred immobilizing agents such as the $C_{16}$–$C_{18}$ fatty alcohols increase the rate of crystallization of the lotion causing the lotion to crystallize rapidly onto the surface of the substrate. Lower lotion levels can therefore be utilized or a superior lotion feel can be delivered. Traditionally, greater amounts of lotion were needed to generate softness because of the flow of these liquids into the diaper core.

Other types of immobilizing agents can be used either alone or in combination with the fatty alcohols, fatty acids, and fatty alcohol ethoxylates described above. Examples of these other types of immobilizing agents includes polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using diaper topsheets to which the lotion composition is applied, these esters and amides should also be relatively mild and non-irritating to the skin.

Suitable polyhydroxy fatty acid esters for use in the present invention will have the formula:

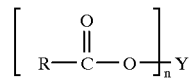

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-o etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and trimesters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di- strearate and sucrose mono- and di- laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl , most preferably Cl alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH$(CH_2OH)$—$[(CHOH)_{n-1}]$—$CH_2OH$, —$CH_2OH$—$CH_2$—$(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl, $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

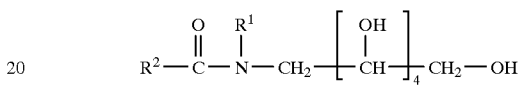

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3$ $(CH_2)_{17}$ $(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, beeswax, candelilla, paraffin, ceresin, esparto, ouricuri, rezowax, and other known waxes. Preferably the wax is a paraffin wax. An example of a particularly preferred paraffin wax is Parrafin S.P. 434 from Strahl and Pitsch Inc. P.O. Box 1098 West Babylon, N.Y. 11704.

The amount of immobilizing agent that should be included in the lotion composition will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 90% of the immobilizing agent. Preferably, the lotion composition comprises from about 5 to about 50%, most preferably from about 10 to about 40%, of the immobilizing agent.

3. Optional Hydrophilic Surfactant

As mentioned above, it is highly desirable that the diaper topsheet is made of a hydrophilic material to promote rapid transfer of liquids (e.g., urine) through the topsheet. Similarly, it is important that the lotion composition also be sufficiently wettable to ensure that liquids will transfer through the topsheet more rapidly. This diminishes the likelihood that body exudates will flow off the lotion coating rather than being drawn through the topsheet and being absorbed by the absorbent core. Depending upon the particular immobilizing agent used in the lotion composition of the present invention, an additional hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 will require addition of hydrophilic surfactant to improve wettability when the lotion composition is applied to diaper topsheets. Similarly, a hydrophobic emollient such as petrolatum will require the addition of a hydrophilic surfactant.

Suitable hydrophilic surfactants will be miscible with the emollient and the immobilizing agent so as to form homogeneous mixtures. Because of possible skin sensitivity of those using disposable absorbent products to which the lotion composition is applied, these surfactants should also be relatively mild and non-irritating to the skin. Typically, these hydrophilic surfactants are nonionic to be not only non-irritating to the skin, but also to avoid other undesirable effects on any underlying tissue laminate structure, e.g., reductions in tensile strength.

Suitable nonionic surfactants may be substantially non-migratory after the lotion composition is applied to the diaper topsheets and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in lotion compositions of the present invention include alkylglycosides; alkylglycoside ethers as described in U.S. Pat. No. 4,011,389 (Langdon, et al), issued Mar. 8, 1977; alkylpolyethoxylated esters such as Pegosperse 1000 MS (available from Lonza, Inc., Fair Lawn, N.J.), ethoxylated sorbitan mono-, di- and/or trimesters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5 T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 ( i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to increase the wettability of the lotion composition to a desired level will depend upon the HLB value and level of immobilizing agent used, the HLB value of the surfactant used and like factors. The lotion composition can comprise from about 1 to about 50% of the hydrophilic surfactant when needed to increase the wettability properties of the composition. Preferably, the lotion composition comprises from about 1 to about 25%, most preferably from about 10 to about 20%, of the hydrophilic surfactant when needed to increase wettability.

4. Other Optional Components

Lotion compositions can comprise other optional components typically present in emollient, creams, and lotions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed in appropriate amounts in the lotion compositions of the present invention.

C. Treating Diaper Topsheets With Lotion Composition

In preparing lotioned diaper products according to the present invention, the lotion composition is applied to the outer surface (i.e., body facing surface) of a diaper topsheet. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the diaper topsheet.

The manner of applying the lotion composition to the diaper topsheet should be such that the topsheet does not become saturated with the lotion composition. If the topsheet becomes saturated with the lotion composition, there is a greater potential for the lotion to block the topsheet openings, reducing the ability of the topsheet to transmit fluid to the underlying absorbent core. Also, saturation of the topsheet is not required to obtain the therapeutic and/or protective lotion benefits. Particularly suitable application methods will apply the lotion composition primarily to the outer surface of the diaper topsheet.

The minimum level of lotion to be applied to the diaper topsheets is an amount effective for reducing the adherence of BM to the skin of the wearer. The lotion composition is preferably applied to the diaper topsheets of the present invention in an amount ranging from about 0.1 mg/in$^2$ to about 25 mg/in$^2$ more preferably from about 1 mg/in$^2$ to about 10 mg/in$^2$ (mg of lotion per square inch of coated topsheet). Because the emollient is substantially immobilized on the surface of the topsheet, less lotion composition is needed to impart the desired skin care benefits. Such relatively low levels of lotion composition are adequate to impart the desired therapeutic and/or protective lotion benefits to the topsheet, yet do not saturate the topsheet's absorbency and/or wettability properties.

The lotion composition may be applied to the entire surface of the topsheet or portions thereof. Preferably, the lotion composition is applied in a stripe aligned with and centered on the longitudinal centerline of the disposable absorbent article. Most preferably, as described in the Examples hereinafter, the lotion composition is applied to a discrete version of the topsheet, e.g., a 3.75 inch wide (diaper lateral direction) and 7 inch long (diaper longitudinal direction) patch generally disposed toward the second waist region.

The lotion composition can also be applied nonuniformly to the outer surface of the diaper topsheet. By "nonuniform" is meant that the amount, pattern of distribution, etc. of the lotion composition can vary over the topsheet surface. For example, some portions of the treated surface of the topsheet can have greater or lesser amounts of lotion composition, including portions of the surface that do not have any lotion composition on it.

The lotion composition can be applied to the topsheet at any point during assembly. For example, the lotion composition can be applied to the topsheet of the finished disposable absorbent product before it has been packaged. The lotion composition can also be applied to the topsheet before it is combined with the other raw materials to form a finished disposable absorbent product.

The lotion composition is typically applied from a melt thereof to the diaper topsheet. Since the lotion composition melts at significantly above ambient temperatures, it is usually applied as a heated coating to the topsheet. Typically, the lotion composition is heated to a temperature in the range from about 35° to about 100° C., preferably from 40° to about 90° C., prior to being applied to the diaper topsheet. Once the melted lotion composition has been applied to the diaper topsheet, it is allowed to cool and solidify to form solidified coating or film on the surface of the topsheet. Preferably, the application process is designed to aid in the cooling/set up of the lotion.

In applying lotion compositions of the present invention to diaper topsheets, spraying, gravure coating and extrusion coating methods are preferred. FIG. 1 illustrates one such preferred method involving spraying of the coating on the diaper topsheet before the topsheet is assembled with the other raw materials into a finished product. Referring to FIG. 1, a nonwoven topsheet web 1 is unwound from parent topsheet roll 2 (rotating in the direction indicated by arrow 2a) and advanced to spray station 6 where one side of the web is sprayed with a hot, molten (e.g., 65° C.) lotion composition. After leaving spray station 6, nonwoven topsheet web 1 becomes a lotioned topsheet web indicated by 3. Lotioned topsheet web 3 is then advanced around turning roll 4 and turning roll 8, and then wound up on lotioned topsheet parent roll 10 (rotating in the direction indicated by arrow 10a).

Figure 2:
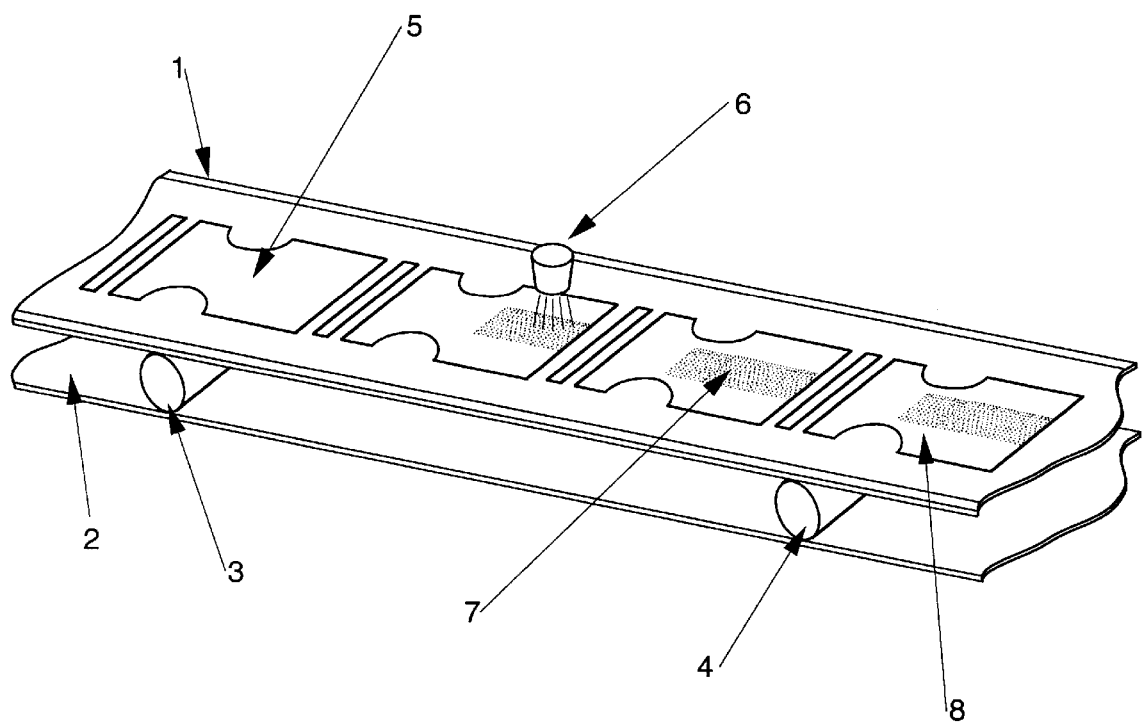
FIG. 2 is a schematic representation illustrating an alternative process for applying the lotion composition of the present invention to diaper topsheets.

FIG. 2 illustrates an alternative preferred method involving continuous or intermittent spraying of the lotion composition on to a diaper topsheet during the converting operation. Referring to FIG. 2, conveyor belt 1 advances in the direction shown by the arrows on turning rolls 3 and 4 and becomes returning conveyor belt 2. Conveyor belt 1 carries nonlotioned diaper 5 to spray station 6 where topsheet patch 7 is sprayed with a hot, molten (e.g., 65° C.) lotion composition. After leaving spray station 6, nonlotioned diaper 5 becomes lotioned diaper 8 having a lotioned topsheet. The amount of lotion composition transferred to topsheet patch 7 is controlled by: (1) the rate at which the molten lotion composition is sprayed from spray station 6; and/or (2) the speed at which conveyor belt 1 travels under spray station 6.

Specific Illustrations of the Preparation of Lotioned Diaper Topsheets According to the Present Invention The following are specific illustrations of treating diaper topsheets with lotion compositions in accordance with the present invention:

EXAMPLE 1

A. Preparation of Lotion Compositions

A water free lotion composition (Lotion A) is made by mixing the following melted (i.e., liquid) components together: Mineral Oil (Carnation White Mineral Oil, USP made by Witco Corp.), Cetearyl Alcohol (a mixed linear $C_{16}$–$C_{18}$ primary alcohol made by the Procter & Gamble Company under the name TA-1618); Steareth-2 (Brij 72, a $C_{18}$ linear alcohol ethoxylate having an average degree of ethoxylation of 2, made by ICI America). The weight percentages of these components are shown in Table I below:

TABLE I

| Component | Weight % |
|---|---|
| Mineral Oil | 50 |
| Cetearyl Alcohol | 35 |
| Steareth-2 | 15 |

B. Preparation of Lotioned Diaper Topsheet by Hot Melt Spraying

Lotion Composition A is placed into a heated tank operating at a temperature of 125° F. The composition is subsequently sprayed (using a Dynatec E84B1758 spray head, operating at a temperature of 165° F. and an atomization pressure of 2.40 psig) onto the topsheet of a diaper in a 3.75 inch wide (diaper lateral direction) and 7 inch long (diaper longitudinal direction) area, the patch beginning 1 inch forward of the lateral centerline and extending toward the rear of the product. Add-on level=0.006 g/in$^2$(9.3 g/m$^2$).

EXAMPLE 2

The lotion composition A (prepared in accordance with the procedure in Example 1) is subsequently sprayed onto the topsheet of a diaper in a 3.75 inch wide (diaper lateral direction) stripe centered on the longitudinal centerline and extending the entire length of the product. Add-on level= 0.006 g/in$^2$(9.3 g/m$^2$).

EXAMPLE 3

The lotion composition A (prepared in accordance with the procedure in Example 1) is subsequently sprayed onto the topsheet of a diaper in a 3.75 inch wide (diaper lateral direction) stripe centered on the longitudinal centerline and 7 inch long (diaper longitudinal direction) area, the patch beginning 1 inch forward of the lateral centerline and extending toward the rear of the product. Add-on level= 0.003 g/in$^2$(4.65 g/m$^2$).

EXAMPLE 4

A. Preparation of Lotion Compositions

A water free lotion composition (Lotion B) is made by mixing the following melted (i.e., liquid) components together: Mineral Oil (Carnation White Mineral Oil, USP made by Witco Corp.), and Cetearyl Alcohol (a mixed linear $C_{16}$–$C_{18}$ primary alcohol made by the Procter & Gamble Company under the name TA-1618). The weight percentages of these components are shown in Table II below:

TABLE II

| Component | Weight % |
|---|---|
| Mineral Oil | 65 |
| Cetearyl Alcohol | 35 |

B. Preparation of Lotioned Tissue by Hot Melt Spraying

Lotion Composition B is placed into a heated tank operating at a temperature of 125° F. The composition is subsequently sprayed (using a Dynatec E84B1758 spray head, operating at a temperature of 165° F. and an atomization pressure of 2.40 psig) onto the topsheet of a diaper in a 3.75 inch wide (diaper lateral direction) and 7 inch long (diaper longitudinal direction) area, the patch beginning 1 inch forward of the lateral centerline and extending toward the rear of the product. Add-on level=0.006 g/in$^2$(9.3 g/m$^2$).

EXAMPLE 5

A. Preparation of Lotion Composition

A water free lotion composition (Lotion C) is made by mixing the following melted (i.e., liquid) components together: White Protopet® 1S (white petrolatum made by Witco Corp.), Cetearyl Alcohol (a mixed linear $C_{16}$–$C_{18}$ primary alcohol made by the Procter & Gamble Company under the name TA-1618); Steareth-2 (Brij 762, a $C_{18}$ linear alcohol ethoxylate having an average degree of ethoxylation of 2 made by ICI America). The weight percentages of these components are shown in Table I below:

A water free lotion composition (Lotion C) is made by mixing together the following melted (i.e., liquid) components in the weight percentages shown in the Table III below according to the procedure of Example 2:

TABLE III

| Component | Weight % |
|---|---|
| White Protopet ® 1S | 50 |
| Cetearyl Alcohol | 35 |
| Steareth-2 | 15 |

B. Preparation of Lotioned Tissue by Hot Melt Spraying

Lotion Composition C is placed into a heated tank operating at a temperature of 125° F. The composition is subsequently sprayed (using a Dynatec E84B1758 spray head, operating at a temperature of 165° F. and an atomization pressure of 2.40 psig) onto the topsheet of a diaper in a 3.75 inch wide (diaper lateral direction) and 7 inch long (diaper longitudinal direction) area, the patch beginning 1 inch forward of the lateral centerline and extending toward the rear of the product. Add-on level=0.006 g/in$^2$(9.3 g/m$^2$).

EXAMPLE 6

A. Preparation of Lotion Composition

A water free lotion composition (Lotion D) is made by mixing the following melted (i.e., liquid) components together: White Protopet® 1S (white petrolatum made by Witco Corp.); Dow Corning 556 Cosmetic Grade Fluid(a polyphenylmethylsiloxane made by the Dow Corning Corporation), An example of a particularly preferred paraffin wax is Parrafin S.P. 434 (a paraffin wax made by Strahl and Pitsch Inc.); Cetearyl Alcohol (a mixed linear $C_{16}$–$C_{18}$ primary alcohol made by the Procter & Gamble Company under the name TA-1618); PEG 2000 (a polyethylene glycol having a MW of 2000 made by Sigma-Aldrich Corp). The weight percentages of these components are shown in Table IV below:

TABLE IV

| Component | Weight % |
| --- | --- |
| White Protopet ® 1S | 52 |
| Polyphenylmethylsiloxane | 20 |
| Paraffin Wax | 15 |
| Cetearyl Alcohol | 10 |
| PEG 2000 | 3 |

B. Preparation of Lotioned Tissue by Hot Melt Spraying

Lotion Composition D is placed into a heated tank operating at a temperature of 150° F. The composition is subsequently sprayed (using a Dynatec E84B1758 spray head, operating at a temperature of 170° F. and an atomization pressure of 2.40 psig) onto the topsheet of a diaper in a 3.75 inch wide (diaper lateral direction) and 7 inch long (diaper longitudinal direction) area, the patch beginning 1 inch forward of the lateral centerline and extending toward the rear of the product. Add-on level=0.006 g/in$^2$(9.3 g/m$^2$).

What is claimed is:

1. An absorbent article comprising:
   A) a liquid impervious backsheet;
   B) a liquid pervious topsheet joined to said backsheet, said topsheet having an inner surface oriented toward the interior of said absorbent article and an outer surface oriented toward the skin of the wearer when said absorbent article is being worn, wherein at least a portion of said topsheet outer surface comprises an effective amount of a lotion coatings which is semi-solid or solid at 20° C. said lotion coating comprising:
      (i) from about 10 to about 95% of a substantially water free emollient having a plastic or fluid consistency at 20° C. wherein said emollient contains 5% or less water, said emollient comprising a member selected from the group consisting of petroleum-based emollients, fatty acid ester emollients, alkyl ethoxylate emollients, and mixtures thereof;
      (ii) from about 5 to about 90% of an agent capable of immobilizing said emollient on said outer surface of the topsheet, said immobilizing agent being miscible with said emollient, said immobilizing agent having a melting point of at least about 35° C. wherein said immobilizing agent is selected from the group consisting of polyhydroxy fatty acid esters, polyhydroxy fatty acid amides, $C_{14}$–$C_{22}$ fatty alcohols, $C_{12}$–$C_{22}$ fatty acids, $C_{12}$–$C_{22}$ fatty alcohol ethoxylates, and mixtures thereof; and
   C) an absorbent core positioned between said topsheet and said backsheet.

2. The absorbent article of claim 1 wherein said article is a sanitary napkin.

3. The absorbent article of claim 1 wherein said emollient contains about 5% or less water and comprises a petroleum based emollient selected from the group consisting of mineral oil, petrolatum, and mixtures thereof.

4. The absorbent article of claim 3 wherein said emollient is petrolatum.

5. The absorbent article of claim 4 wherein said emollient is mineral oil.

6. The absorbent article of claim 1 wherein the quantity of lotion coating on said portion of said topsheet outer surface ranges from about 0.1 mg/in$^2$ to about 25 mg/in$^2$.

7. The absorbent article of claim 6 wherein the quantity of lotion coating on said portion of said topsheet outer surface ranges from about 1 mg/in$^2$ to about 10 mg/in$^2$.

8. The absorbent article of claim 1 wherein said emollient comprises a fatty acid ester emollient selected from the group consisting of methyl palmitate, methyl stearate, isopropyl laurate, isopropyl myristate, isopropyl paimitate, ethylhexyl palmitate, lauryl lactate and cetyl lactate, and mixtures thereof.

9. The absorbent article of claim 1 wherein said emollient comprises an alkyl ethoxylate emollient selected from the group consisting of $C_{12}$–$C_{18}$ fatty alcohol ethoxylates having an average degree of ethoxylation ranging from about 2 to about 30.

10. The absorbent article of claim 1 wherein said lotion coating comprises from about 5 to about 50% of said immobilizing agent, said immobilizing agent having a melting point of at least about 40° C.

11. The absorbent article of claim 10 wherein said immobilizing agent comprises a $C_{14}$–$C_{22}$ fatty alcohol.

12. The absorbent article of claim 11 wherein said immobilizing agent comprises a $C_{16}$–$C_{18}$ fatty alcohol selected from the group consisting of cetyl alcohol, stearyl alcohol, and mixtures thereof.

13. The absorbent article of claim 10 wherein said immobilizing agent comprises a polyhydroxy fatty acid ester having the formula:

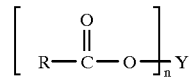

wherein R is a $C_5$–$C_{31}$ hydrocarbyl group; Y is a polyhydroxyhydrocarbyl moiety having a hydrocarbyl chain with at least 2 free hydroxyls directly connected to the chain; and n is at least 1.

14. The absorbent article of claim 13 wherein said immobilizing agent comprises a polyhydroxy fatty acid ester selected from the group consisting of sorbitan esters of $C_{16}$–$C_{22}$ saturated fatty acids, glyceryl monoesters of $C_{16}$–$C_{22}$ saturated fatty acids, and sucrose esters of $C_{12}$–$C_{22}$ saturated fatty acids.

15. The absorbent article of claim 14 wherein said immobilizing agent comprises a polyhydroxy fatty acid ester selected from the group consisting of sorbitan palmitates, sorbitan stearates, sorbitan behenates, glyceryl monostearate, glyceryl monopalmitate, glyceryl monobehenate, sucrose mono- and di- stearate, and sucrose mono- and di- laurate.

16. The absorbent article of claim 15 wherein said immobilizing agent comprises sorbitan stearates.

17. The absorbent article of claim 10 wherein said immobilizing agent comprises a polyhydroxy fatty acid amide having the formula:

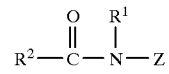

wherein $R^1$ is $C_1$–$C_4$ hydrocarbyl, 2-hydroxyethyl, 2-hydroxypropyl, methoxyethyl, methoxypropyl or a mixture thereof; $R^2$ is a $C_5$–$C_{31}$ hydrocarbyl group; and Z is a polyhydroxyhydrocarbyl moiety having a linear hydrocarbyl chain with at least 3 hydroxyls directly connected to the chain.

18. The absorbent article of claim 17 wherein $R^1$ is N-methyl, N-ethyl, N-propyl, N-isopropyl, N-butyl, N-2-hydroxyethyl, N-methoxypropyl or N-2-hydroxypropyl; $R^2$ is straight chain $C_{11}$–$C_{17}$ alkyl or alkenyl, or mixture thereof, and Z is glycityl.

19. The absorbent article of claim 18 wherein said immobilizing agent comprises a polyhydroxy fatty acid amide selected from the group consisting of N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl, glucamide, N-tallowyl-N-methyl glucamide, and N-tallowyl-N-methoxypropyl glucamide.

20. The absorbent article of claim 10 wherein said immobilizing agent comprises a paraffin wax.

21. The absorbent article of claim 1 wherein said lotion coating further comprises from about 1 to about 50% of a hydrophilic surfactant, said hydrophilic surfactant having an HLB value of at least about 4.

22. The absorbent article of claim 21 wherein said lotion coating further comprises from about 1 to about 25% of said hydrophilic surfactant, said hydrophilic surfactant being nonionic and having an HLD value of from about 4 to about 20.

23. The absorbent article of claim 22 wherein said hydrophilic surfactant comprises an ethoxylated alcohol having an alkyl chain of from about 8 to about 22 carbon atoms and having an average degree of ethoxylation ranging from about 1 to about 54.

24. The absorbent article of claim 23 wherein said ethoxylated alcohol has an alkyl chain of from about 11 to about 22 carbon atoms and having an average degree of ethoxylation ranging from about 2 to about 30.

25. The absorbent article of claim 24 wherein said hydrophilic surfactant comprises an ethoxylated sorbitan ester of a $C_{12}$–$C_{18}$ fatty acid having an average degree of ethoxylation of from about 2 to about 20.

* * * * *

UNITED STATES PATENT AND TRADEMARK OFFICE
CERTIFICATE OF CORRECTION

PATENT NO.    : 5,968,025
DATED         : October 19, 1999
INVENTOR(S)   : Roe et al.

It is certified that error appears in the above-identified patent and that said Letters Patent is hereby corrected as shown below:

Column 3,
Lines 9 and 11, please delete "articles" and insert therefor -- article --.
Line 46, after "conditions.", please insert a carriage return and tab (to start a new paragraph), and delete "importantly" and insert therefor -- Importantly --.

Column 5,
Line 14, please delete "wearers" and insert therefor -- wearer's --.

Column 9,
Line 20, please delete "wearers" and insert therefor -- wearer's --.
Line 55, please delete "semisolid solid" and insert therefor -- semi-solid --.
Line 56, after "the", please insert -- lotion --.

Column 10,
Line 6, (last line of the table), $2^{nd}$ column, please delete "$\geq 35$" and insert therefor -- $\geq 38$ --.
Line 17, please delete "wearers" and insert therefor -- wearer's --.

Column 11,
Line 46, please delete "thoxylate" and insert therefor -- ethoxylate --.

Column 12,
Line 54, please delete "polysiloxanes" and insert therefor -- polysiloxane --.

Column 15,
Line 4, please delete "tri-o", and insert therefor -- tri- --.
Line 18, please delete "trimesters" and insert therefor -- tri-esters --.
Line 34, please delete "di-strearate" and insert therefor -- di-stearate --.

Column 16,
Line 8, after "N-2-hydroxypropyl", please delete "," (the comma) and insert therefor -- . -- (a period).
Line 41, please delete "$CH_3 \ (CH_2)_{17}$" and insert therefor -- $CH_3(CH_2)_{17}$ --.

Column 17,
Line 55, please delete "1000 MS" and insert therefor -- 1000MS --.
Line 57, please delete "trimesters" and insert therefor -- tri-esters --.

UNITED STATES PATENT AND TRADEMARK OFFICE
CERTIFICATE OF CORRECTION

PATENT NO. : 5,968,025
DATED : October 19, 1999
INVENTOR(S) : Roe et al.

It is certified that error appears in the above-identified patent and that said Letters Patent is hereby corrected as shown below:

Column 22,
Line 59, please delete "Coming" and insert therefor -- Corning --.

Column 23,
Line 31, please delete "coatings" and insert therefor -- coating --.
Lines 32 and 35, after "20° C.", please insert -- , -- (a comma).

Column 24,
Line 4, please delete "paimitate," and insert therefor -- palmitate --.
Line 57, please delete "$R^1$ is HX $C_1$-$C_4$" and insert therefor -- $R^1$ is H, $C_1$-$C_4$ --.
Line 67, after "thereof", please delete "," and insert therefor -- ; -- (a semi-colon).

Column 26,
Line 2, please delete "HLD" and insert therefor -- HLB --.

Signed and Sealed this

Thirteenth Day of July, 2004

JON W. DUDAS
*Acting Director of the United States Patent and Trademark Office*